(12) United States Patent
Wen et al.

(10) Patent No.: US 7,132,015 B2
(45) Date of Patent: Nov. 7, 2006

(54) MATERIALS FOR DENTAL AND BIOMEDICAL APPLICATION

(75) Inventors: Hai Bo Wen, Warsaw, IN (US); Janet Moradian-Oldak, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 554 days.

(21) Appl. No.: 10/371,678

(22) Filed: Feb. 20, 2003

(65) Prior Publication Data

US 2003/0170378 A1   Sep. 11, 2003

Related U.S. Application Data

(60) Provisional application No. 60/358,157, filed on Feb. 20, 2002.

(51) Int. Cl.
*C30B 7/00* (2006.01)
(52) U.S. Cl. .......................................... 117/68; 117/75
(58) Field of Classification Search .................. 117/68, 117/75
See application file for complete search history.

(56) References Cited

U.S. PATENT DOCUMENTS

| 5,609,633 A | 3/1997 | Kokubo |
| 5,612,049 A | 3/1997 | Li et al. |
| 6,051,272 A | 4/2000 | Stupp et al. |
| 6,139,585 A | 10/2000 | Li |

OTHER PUBLICATIONS

Aoba, T., et al., "Selective Adsorption of Porcine-Amelogenins onto Hydroxyapatite and their Inhibitory Activity on Hydroxyapatite Growth in Supersaturated Solutions", *Calcified Tissue International*, 1987, 41, pp. 281-289.

Ausubel, F.M., et al., "Commercially Available Software", *Current Protocols in Molecular Biology*, eds., 1987 Supplement 30, Section 7.7.18, Table 7.7.1.

Berman, A., et al., "Biological Control of Crystal Texture: A Widespread Strategy for Adapting Crystal Properties to Function", *Science*, 1993, 259, pp. 776-779.

Brookes, S.J., et al., "Biochemistry and Molecular Biology of Amelogenin Proteins of Developing Dental Enamel", *Archs Oral Biol.*, 1995, 40:1, pp. 1-14.

(Continued)

*Primary Examiner*—Felisa Hiteshew
(74) *Attorney, Agent, or Firm*—Malcolm K. McGowan; Bingham McCutchen LLP

(57) ABSTRACT

The invention provides novel dental enamel inspired materials for biomedical and dental applications. The materials are apatite-like calcium phosphate complexes and may comprise apatite, octacalcium phosphate crystals, or mixtures thereof. In one embodiment, the materials (calcium phosphate coatings) are mixtures of crystals of apatite and its precursor, octacalcium phosphate, nucleated on a titanium surface. They are prepared using a chemical process leading to the formation of biological apatite which is similar to that found in natural bone and teeth. In one embodiment, the materials are prepared by placing a titanium substrate in a supersaturated calcifying solution containing native or purified recombinant amelogenins. The presence of the amelogenins modulates apatite crystal growth to mimic in vivo apatite crystal formation. Applications for the materials include, without limitation, dental tissue (enamel, dentin, cementum) replacement, orthopeadic implants for bone repair, and coatings for improving the biocompatibility and bone regeneration capability of currently available implants or medical devices made of metallic, polymeric, ceramic or composite materials.

2 Claims, 7 Drawing Sheets

OTHER PUBLICATIONS

Brown, "Session V, General Comment", *J. Dent. Res. Special Issue B*, 1979, pp. 857-860.

Brown, W.E., "Octacalcium Phosphate and Hydroxyapatite", *Nature*, 1962, 196:4859, pp. 1048-1050.

Damien, C. J., et al., "Bone Graft and Bone Graft Substitutes: A Review of Current Technology and Applications", *Journal of Applied Biomaterials*, 1991, 2:3, pp. 187-208.

Diekwisch, T., et al., "Initial enamel crystals are not spatially associated with mineralized dentine", *Cell & Tissue Research*, 1995, 279, pp. 149-167.

Doi, Y., et al., "Inhibition of Seeded Growth of Enamel Apatite Crystals", *J. Dent. Res.*, 1984, 63:2, pp. 98-105.

Eastoe, J.E., "Enamel Protein Chemistry—Past, Present and Future", *J. Dent. Res. Special Issue B*, 1979, vol. 58(B), pp. 753-763.

Finchem, A.G., et al., "Amelogenin Post-Secretory Processing During Biomineralization in the Postnatal Mouse Molar Tooth", *Archs Oral Bio.*, 1991, 36:4, pp. 305-317.

Finchem, A.G., et al., "Amelogenin Post-Translational Modifications: Carboxy-Terminal Processing and the Phosphorylation of Bovine and Porcine 'Trap' and 'LRAP' Amelogenins", *Biochemical and Biophysical Research Communications*, 1993, 197:1, pp. 248-255.

Finchem, A.G., et al., "Amelogenin proteins of developing dental enamel", *Dental Enamel: Ciba Foundation Sumposium 205*, 1997, pp. 118-134.

Fincham, A.G., "Comparative Mass Spectrometric Analyses of Enamel Matrix Proteins from Five Species Suggest a Common Pathway of Post-Secretory Proeteolytic Processing", *Connective Tissue Research*, 1996, 35:1-4, 151-156 [205-210].

Finchem, A.G., et al., "Evidence for Amelogenin 'Nanospheres' as Functional Components of Secretory-Stage Enamel Matrix", *Journal of Structural Biology*, 1995, 115, pp. 50-59.

Finchem, A.G., et al., "Self-Assembly of a Recombinant Amelogenin Protein Generates Supramolecular Structures", *Journal of Structural Biology*, 1994, 112, pp. 103-109.

Finchem, A.G., et al., "The Structural Biology and the Developing Dental Enamel Matrix", *J. Structural Biology*, 1999, 126, pp. 270-299.

Gibson, C.W., et al., "Identification of the Leucine-Rich Amelogenin Peptide (LRAP) as the Translation Product of an alternatively Spliced Transcript", *Biochemical and Biophysical Research Communication*, 1991, 174:3, pp. 1306-1312.

Gilman, H., et al., "Seeded Growth of Hydroxyapatite in the Presence of Dissolved Albumin at Constant Composition", *Journal of Inorganic Biochemistry*, 1994, 55, pp. 31-39.

Hench, L.L., "Bioactive Ceramics: Theory and Clinical Applications", Bioceramics, 1994, 7, edited by Ö.H. Andersson, and A. Yli-Urpo, Butterworth-Heinemann Ltd., Oxford, 3, *Proceedings of the 7th International Sumposium on Ceramics in Medicine*, turku, Finaldn, Jul. 1994).

Hench, L.L., "Bioceramics", *J. Am. Ceram. Soc.*, 1998, , 81, 1705-1728.

Hench, L.L., et al., "Biological Applications of Bioactive glasses", *Life Chem. Rep.*, 1996, 13, pp. 187-241.

Heuer, A.H., et al., 1992, "Innovative Materials Processing Strategies: A Biomimetic Approach," *Science*, 255, pp. 1098-1105.

Hunter, G.K., et al., Effects of Recombinant Amelogenin on Hydroxyapatite Formation *In Vitro*, *Calcif Tissue Int*, 1999, 65, pp. 226-231.

Iijima, M., et al., "Effects of bovine amelogenins on the crystal morphology of octacalcium phosphate in a model system of tooth enamel formation," 2001, *J. Crystal Growth*, 222, pp. 615-626.

Iijima. M., et al., "Elongated Growth of Octacalcium Phosphate Crystals in Recombinant Amelogenin Gels Under Controlled Ionic Flow", *J. Dent. Res.*, 2002, 81:1, pp. 69-73.

Katsura, N., "Nanospace Theory for Biomineralization", Chapter 2.12, Department of Oral Biochemistry, School of Dentistry, Nagasaki University, Nagasaki, 852, Japan, pp. 193-197.

Moradian-Oldak, J. "Amelogenins: assembly, processing and control of crystal morphology", *Matrix Biology*, 2001, 20, pp. 293-305.

Moradian-Oldak, J., et al., "Detection of Monodisperse Aggregates of a Recombinant Amelogenin by Dynamic Light Scattering", *Bioploymers*, 1994, 34, pp. 1339-1347.

Mordian-Oldak, J., et al., "Interaction of Amelogenin with Hydroxyapatite Crystals: An Adherence Effect Through Amelogenin Molecular Self-Association", *Biopolymers*, 199846, pp. 225-238.

Moradian-Oldak, J., et al., "Self-Assembly Properties of Recombinant Engineered Amelogenin Proteins Analyzed by Dynamic Light Scattering and Atomic Force Microscopy", *Journal of Structural Biology*, 2000, 131, pp. 27-37.

Moradian-Oldak, J., et al., "Temperature and pH-Dependent Supramolecular Self-Assembly of Amelogenin Molecules: A Dynamic Light-Scattering Analysis", *Journal of Structural Biology*, 1998, 122, pp. 320-327.

Rabin, S., et al., "Effect of serum proteins on solution-induced surface transformations of bioactive ceramics", *Journal of Biomedical Materials Research*, 1996, 30, pp. 273-279.

Robinson, C., et al., "The Role of Albumin in Developing Rodent Dental Enamel: A Possible Explanation for White Spot Hypoplasia", *J Dent Res*, 1992, 71:6, pp. 1270-1274.

Ryu, O.H., et al., "Characterization of Recombinant Pig Enamelysin Activity and Cleavage of Recombinant Pig and Mouse Amelogenins", *J. Dent Res*, 1999, 78:3, pp. 743-750.

Simmer, J.P., "Isolation and Characterization of a Mouse Amelogenin Expressed in *Escherichia coli*", *Calcif Tissue Int*, 1994, 54, pp. 312-319.

Snead, M.L., "DNA Sequence for Cloned cDNA for Murine Amelogenin Reveal the Amino Acid Sequence for Enamel-Specific Protein", *Biochemical and Biophysical Research Communications*, 1985, 129:3, pp. 812-818.

Tan, J., et al., "Quantitative Analysis of Amelogenin Solubility", *J. Dent. Res.*, 1998, 77:6, pp. 1388-1396.

Termine, J.D., et al., "Properties of Dissociatively Extracted Fetal Tooth Matrix Proteins", *J. Biol. Chem.*, 1980, 255:20, pp. 9760-9768.

Veis, A. et al., "Specific Amelogenin Gene Splice Products Have Signaling Effects on Cells in Culture and in Implants *in vivo*," *J. Biological Chemistry*, 2000, 275:52, pp. 41263-41272.

Weiner S., et al., "The Material Bone: Structure-Mechanical Function Relations", *Annu. Rev. Mater. Sci.*, 1998, 38, pp. 271-298.

Wen, H.B., et al. "Crystal growth of calcium phosphate on biomaterials", *Recent Res. Devel. Crystal Growth Res.*, 1999, 1, pp. 51-65.

Wen, H.B., et al., "Crystal growth of calcium phosphate on chemically treated titanium", *Journal of Crystal Growth*, 1998, 186, pp. 616-623.

Wen, H.B., et al., "Dose-dependent Modulation of Octacalcium Phosphate Crystal Habit by Amelogenins", *J. Dent Res*, 2000, 79:11, pp. 1902-1906.

Wen, H.B., et al., "Effects of amelogenin proteins on calcium phosphate crystal growth on biomaterials", *Research Signpost, 37/661(2) Fort P.O., Trivandrum-695 023 Kerala, India; Biomimetic Calcium Phosphase Coatings, 2002*:ISBN:81-7736-090-6, pp. 55-68.

Wen, H.B., et al., "Effects of amelogenin on OCP and Apatite Crystal Growth on Titanium",Transactions of the 27 Annual Meeting of the Society for Biomaterials, 2001, 24, p. 100.

Wen, H.B., et al., "Effects of amelogenin on the transforming surface microstructures of Bioglass in the calcifying solution", *J. Biomed Mater Res*, 2000, 52, pp. 762-773.

Wen, H.B., et al., "Incorporation of bovine serum albumin in calcium phosphate coating on titanium", *J. Biomed Mater Res*, 1999, 46, pp. 245-252.

Wen, H.B., et al., "Modification of calcium-phosphate coatings on titanium by recombinant amelogenin", *J. Biomed Mater Res*, 2003, 64A, pp. 483-490.

Wen, H.B., et al., "Modulation of apatite crystal growth on Bioglass by recombinant amelogenin" *Biomaterials*, 1999, 20, pp. 1717-1725.

Wen, H.B., et al., "Preparation of bioactive microporous titanium surface by a new two-step chemical treatment", *Journal of Materials Science: Materials in Medicine*, 1998, 9, pp. 121-128.

Wen, H.B., et al., "Progressive accretion of amelogenin molecules during nanospheres assembly revealed by atomic force microscopy", *Matrix Bilogy*, 2001, 20, pp. 387-395.

Zhong, J.P., et al., "Oriented Growth of Hydroxyapatite on Bioglass", *Transactions of the 23rd Annual Meeting of the Society for Biomaterials*, 1997, p. 125.

MATERIALS FOR DENTAL AND BIOMEDICAL APPLICATION

CROSS REFERENCE TO RELATED APPLICATION

This application claims priority under 35 U.S.C. § 119(e) of U.S. Provisional Application Ser. No. 60/358,157, filed Feb. 20, 2002, entitled "Novel Materials for Dental and Biomedical Application." The application is incorporated herein by this reference.

STATEMENT AS TO INVENTION RIGHTS UNDER FEDERALLY SPONSORED RESEARCH

This work was supported by NICDR research grants DE12350 and DE13414. The United States government may have certain rights in the inventions disclosed herein.

BACKGROUND

Biological implants, such as joint and dental prostheses, usually must be permanently affixed or anchored within bone. In some instances it is acceptable to use a bone cement to affix the prosthesis within bone. In the case of many joint prostheses, however, it is now more common to affix the joint prosthesis by encouraging natural bone growth in and around the prosthesis. Bone-to-implant interfaces that result from natural bone ingrowth tend to be stronger over time and more permanent than are bone cement-prosthesis bonds.

Optimal bone ingrowth requires that natural bone grow into and around the prosthesis to be implanted. Bone ingrowth and bone or dental prosthesis fixation can be enhanced by providing irregular beaded or porous surfaces on the implant. Although various materials, including titanium alloys, are biocompatible, they are not necessarily bioactive because they can neither conduct bone formation nor form chemical bonds with bone. Thus, enhanced fixation of implants within bone can be attained by coating the implant with a bioactive mineralized and/or ceramic material. Such coatings have been shown to encourage more rapid bone ingrowth in and around the prosthesis.

Calcium phosphate ceramics, especially hydroxyapatite, have been shown to conduct bone formation. Hydroxyapatite ceramic has been successfully applied as a coating on cementless metallic implants to achieve quick and strong fixation. Thermal plasma spraying is one of the more common methods used to produce hydroxyapatite coatings. However, the resulting plasma-sprayed hydroxyapatite coating is of relatively low density and is not uniform in structure or composition. The adhesion between the coating and substrate is generally not very strong, especially after long term exposure within the body. The generation of hard ceramic particles, resulting from the degradation of thermal plasma sprayed coating, and coating delamination, are major concerns. Also, implants or other polymers with porous structures or complex surfaces are difficult to coat uniformly using line-of-sight temperature plasma spraying.

A general overview of orthopedic implantable materials is given in Damien, Christopher J., and Parsons, Russell J., 1991, Journal of Applied Biomaterials, v2, 187–208. Information related to attempts to address these problems can be found, e.g., in U.S. Pat. Nos. 6,139,585; 6,051,272; 5,609,633; and in some of the publications disclosed herein. Each of these references suffers from one or more of the following disadvantages: weakness, brittleness or unevenness of coatings, a lack of chondrogenic or osteogenic activities, inability to promote the regeneration of periodontal tissues, and the problem of contamination with components which may cause severe immunological reactions.

Thus, a need exists for the production of improved enamel inspired materials which are appropriate for biomedical and dental applications and which overcome the problems discussed above.

SUMMARY

The invention provides an improved method for synthesizing coated implantable articles suitable for biomedical and dental applications. In one embodiment, the method generally comprises the step of contacting an implantable substrate to be coated with a supersaturated calcifying solution, where the solution comprises an effective amount of an amelogenin-type protein. Typically, the substrate will be immersed in the solution under suitable temperature conditions until the desired amount of an enamel-like biomaterial coats the substrate surface. The surface may be coated partially or entirely with the enamel-like biomaterial, depending on the user's preference. Where the coating appears, it is chemically bonded to the surface of the substrate.

The method may be applied to a variety of substrates, including metals, ceramics, polymers and silicon. In particular, the method is useful for coating substrates which are intended for medical implantation, such as bone and dental prostheses. In one embodiment, the substrate may be composed of a strong biocompatible material, for example, a metal such as titanium. In other embodiments, metals including titanium alloy, tantalum, tantalum alloy, stainless steel or cobalt chromium alloy are coated. Other embodiments of the method use well-known biocompatible materials such as ultra high molecular weight polyethylene, hydroxyapatite, Bioglass and Glass Ceramic A-W.

Another embodiment of the invention includes a step in which the metal substrate is activated for crystal growth by a nanometer-scaled porous oxide layer at the metal's surface. One means of achieving such activation is by etching. Many methods of etching are known to those skilled in the art. One useful etching method comprises the steps of contacting the substrate with an effective amount of acid and an effective amount of an oxidizing agent.

In one embodiment of the method of the invention, the substrate to be coated is contacted with a supersaturated calcifying solution comprising calcium phosphate and a buffer which maintains an approximately neutral pH. Typically, the coating reaction is carried out at any temperature between approximately ambient room temperature and a biologically relevant temperature such as the temperature of the human body (i.e., 37 degrees Celsius).

The ionic strength of the supersaturated calcifying solution is between approximately 50 mM and 500 mM. In one embodiment, the ionic strength is between 100 and 200 mM.

In another embodiment, the amelogenin-type protein dissolved in the supersaturated calcifying solution has a function similar to that of mouse amelogenin rM179. In a related embodiment, the amelogenin-type protein comprises the sequence shown in SEQ ID No. 1. The amelogenin-type protein is typically present at concentrations greater than approximately 12.5 µg/ml, including concentrations of 100 µg/ml, or higher.

In other embodiments of the method, the substrate to be coated is exposed to the calcifying solution for approximately an hour or more. The substrate may be exposed to the solution for 24 hours or longer, depending on the thickness or extent of substrate coating desired.

In certain embodiments of the coating method, additional steps are added. For example, in one embodiment, before contacting the substrate with the calcifying solution containing the amelogenin-type protein, the substrate is first contacted with a supersaturated calcifying solution which is substantially free of any amelogenin-type protein.

A further object of the invention is to provide a coating method wherein agents in addition to the amelogenin-type protein are included in the calcifying solution or solutions to which the substrate is exposed. For example, in some embodiments, therapeutic agents such as antibiotics, growth factors, or anti-inflammatory agents are added to the calcifying solution and incorporated into the enamel-like coating.

The amelogenin-type protein of the invention may be incorporated into the enamel-like coating at varying levels depending on parameters such as the concentration of the amelogenin-type protein in the calcifying solution. In some embodiments, the enamel-like coating comprises between $1 \times 10^{-3}\%$ and 1% w/w amelogenin-type protein, although the amounts may vary, for example, to encompass the range from $1 \times 10^{-4}\%$ and 10% w/w amelogenin-type protein.

Another object of the invention is to provide a method for coating an implantable substrate with an enamel-like biomaterial which comprises submicron bundles of elongated apatite crystals with an average aspect ratio (length/width) of at least two.

Yet another object of the invention is to provide a method for modifying the growth of apatite crystals on an implantable substrate. According to one embodiment of this method, crystal growth modification is achieved by the addition of an effective concentration of an amelogenin-type protein to a supersaturated calcifying solution. The substrate on which crystals are grown is then be contacted with the calcifying solution under suitable conditions until the desired growth of crystals is achieved. Typically, the growth of apatite crystals will be modified to produce submicron-sized crystals with an average aspect ratio of approximately two or greater.

This invention also provides the articles produced by the methods described herein.

A further object of the invention is to provide an implantable article which comprises a biocompatible substrate coated with an enamel-like biomaterial. In one variation of this embodiment of the invention, the enamel-like surface coating is chemically bonded to at least a portion of the substrate and comprises apatite crystals and an amelogenin-type protein. In a related embodiment, the crystals are less than 1 μm in length with an average aspect ratio (length to width) of approximately two or greater. In various other embodiments, the crystals which comprise the substrate coating contain carbonate or magnesium in addition to calcium and phosphate, and the calcifying solutions comprise magnesium, sodium, sulfate, chlorine, carbonate or silicate ions, or mixtures thereof.

In a related embodiment, the enamel-like coating of the invention comprises, in addition to amelogenin-type proteins, a therapeutic agent or agents. Such agents include, but are not limited to, growth factors such as, bFGF, aFGF, EGF (epidermal growth factor), PDGF (platelet-derived growth factor), IGF (insulin-like growth factor), TGF-.beta. 1 through 3, including the TGF-.beta. superfamily (BMP's, GDF-5, ADMP-1 and dpp); cytokines, such as various interferons, including interferon-alpha, -beta and -gamma, and interleukin-2 and -3; hormones, such as insulin, growth hormone-releasing factor and calcitonin; non-peptide hormones; antibiotics; anti-cancer agents and chemical agents, such as chemical mimetics of growth factors or growth factor receptors. In certain embodiments, the therapeutic agents include those factors, proteinaceous or otherwise, which are found to play a role in the induction or conduction of growth of bone, ligaments, cartilage or other tissues associated with bone or joints, such as for example, BMP and bFGF.

Yet another object of the invention is to provide a method of enhancing bone ingrowth or soft tissue attachment by implanting an article coated with the enamel-like biomaterial of the invention onto a bone surface or soft tissue. In a related embodiment, the invention provides a method for delivering a therapeutic agent comprising implanting the an article coated with the enamel-like biomaterial of the invention, and further comprising a therapeutic agent, onto a bone surface or soft tissue.

These and other features, aspects, and advantages of the present invention will become better understood with reference to the following description, appended claims, and accompanying drawings.

DETAILED DESCRIPTION

Figure 1:
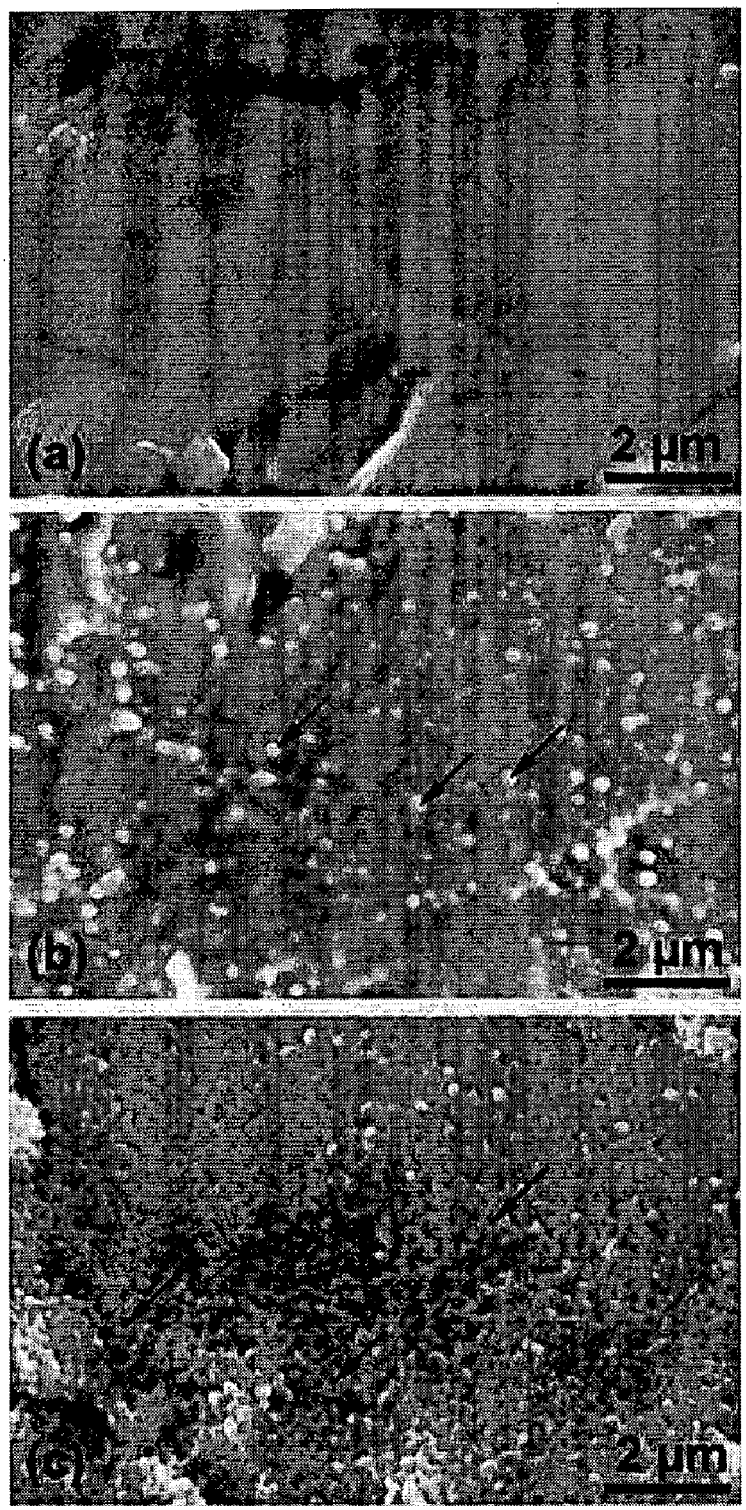
FIG. 1 shows SEM micrographs of titanium surfaces: (a) untreated, (b) HF etching, (c) HF etching and NaOH immersion. Arrows point to nano-sized-structures in (b) and nano-sized-pores in (c).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

As used herein, certain terms have the following defined meanings.

As used in the specification and claims, the singular form "a," "an" and "the" include plural references unless the context clearly dictates otherwise. For example, the term "an article" includes a plurality of articles.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

A "subject" is a vertebrate, preferably an animal or a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation between concentration of amelogin-type protein and crystal formation, it is generally preferable to use a positive control(a sample having a previously determined correlation), and a negative control (a sample lacking amelogin-type protein).

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

All numerical designations, e.g., pH, temperature, time, concentration, and molecular weight, including ranges, are approximations which may be varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

An "effective amount" is an amount sufficient to effect beneficial or desired results. An effective amount can be administered in one or more administrations, applications or dosages.

The invention provides a method for coating articles suitable for dental or prosthetic implantation with an enamel-like biomaterial. The phrase "enamel-like" refers to the similarities to natural enamel, in terms of strength and crystal habit, as well as the bioactive properties of the coating, relative to other synthetic derivatives created without the use of amelogenin-like proteins. The bioactivity of the enamel-like coating manifests itself at least partly in the coating's advantageous ability to promote the ingrowth of natural bone and/or oral tissue around the coated prosthesis. During the natural growth of bone and teeth, a soft extracellular organic matrix serves as a dynamic scaffold to control and facilitate the formation of highly ordered, remarkably elongated carbonated apatite crystals while it is being progressively degraded, leading to a mature enamel composed of more than 95 wt % inorganic minerals (Fincham et al. 1999, J Struct Biol, 122, 320–327). The fusion of natural bone and/or tooth enamel to the coated implants provided by the present invention will provide the implants with greater strength, durability and overall utility.

Without being bound by this proposed mechanism of action, the bioactive properties of the coated inserts produced by the methods of the invention are the result, at least partially, of the presence of amelogenin-type proteins in the calcifying solutions used in the method. Amelogenins are the major protein component of the developing dental enamel, accounting for about 90% of the extracellular organic matrix (Termine et al. 1980, J. Biol. Chem., 255, 9760). The primary structures of amelogenins are highly conserved across species (Fincham et al. 1997, Dental Enamel—Ciba Foundation Symposium 205, D. J. Chadwick, and G. Cardew (Eds.), John Wiley & Sons, Chichester, 118). The parent or full-length amelogenin molecule is comprised of the following three regions: (i) an N-terminal sequence of some 44–45 residues (referred to as TRAP, for Tyrosine-Rich Amelogenin Polypeptide); (ii) a hydrophobic core sequence of some 100–130 residues enriched in proline, leucine, methionine and glutamine; and (iii) an acidic hydrophilic C-terminal sequence of some 15 residues (Fincham et al. 1997, Dental Enamel—Ciba Foundation Symposium 205, D. J. Chadwick, and G. Cardew (Eds.), John Wiley & Sons, Chichester, 118). The hydrophilic C-terminal of the parent amelogenin is proteolytically cleaved shortly after secretion (Fincham et al. 1996, Connect. Tissue Res., 35, 151). Other amelogenin isoforms in the extracellular matrix include the proteolytic product (TRAP) and a few alternative splice products such as the leucine-rich amelogenin polypeptide (LRAP). The term "amelogenin-type proteins" refers to members of this protein family and their natural or synthetic derivatives, for example, as described herein as having the same or similar ability to enhance or modulate crystal formation compared to rM179. One skilled in the art will recognize suitable members of this family according to their amino acid sequences and their effects on bone and/or tooth development in vivo and in vitro. For example, amino acid sequences with 40% or more identity to mouse amelogenin are considered homologs and are expected to have the similar structures and functions.

LRAP is identical to the full-length amelogenin protein at its two termini but lacks a large central segment of the protein (Gibson et al. 1991, Biochem. Biophys. Res. Comm., 174, 1306; Brookes et al. 1995, Archs. Oral Biol., 40, 1). Examples of amino acid sequences of TRAP, LRAP and a recombinant murine amelogenin rM 179 are shown in Table I (Tan et al. 1998, J. Dent. Res., 77, 1388). The full-length rM179 is analogous to the secreted full-length mouse amelogenin M180 lacking only the amino-terminal Met1 and phosphorylation of Ser16. Recombinant rM166 was engineered to create the amelogenin lacking the hydrophilic C-terminal 12 amino acids (Simmer et al. 1994, Calcif. Tissue Int., 54, 312).

TABLE 1

Amino acid sequences of amelogenins.

(M) PLPPHPGSPGYINLSYEVLTPLKWYQSMI$^{30}$

RQPYPSYGYEPMGGW↓LHHQIIPVLSQQHPP$^{60}$
TRAP

SHTLQPHHHLPVVPAQQPVAPQQPMMPVPG$^{90}$

HHSMTPTQHHQPNIPPSAQQPFQQPFQPQA$^{120}$

TABLE 1-continued

Amino acid sequences of amelogenins.

IPPQSHQPMQPQSPLHPMQPLAPQPPLPPL[150]

FSMQPLSPILPELPLEA↓WPATDKTKREEVD[180]
  rM166            rM179

The amino acid sequence of LRAP is underlined. The arrow above "TRAP" indicates the location of the C'-terminal residue of TRAP; the arrow above "rM166" indicates the C'-terminal residue of rM166. rM179 consists of the entire sequence shown above, except for the initiating methionine (shown in parentheses).

Amelogenin proteins have been found to self-assemble in vitro under suitable aqueous conditions to form quasi-spherical quaternary aggregate structures (nanospheres) (Fincham et al. 1995, J. Struct. Biol., 115, 50; Moradian-Oldak et al. 2000, J. Struct. Biol., 131, 27). These nanosphere structures have been postulated to be of great importance in creating an ultrastructural microenvironment for the controlled formation of highly ordered elongated apatite crystals in enamel (Moradian-Oldak 2001, Matrix Biol., 20, 293; Wen et al. 2001, Matrix Biol., 20, 387).

Researchers have attempted to utilize amelogenins to in vitro calcifying systems, which allow the crystal growth of apatite or octacalcium phosphate (OCP) grown from supersaturated calcifying solutions (SCSs) at ambient temperatures. OCP has been proposed to be a potent precursor for natural enamel crystallites (Brown 1979, J. Dent. Res. Special Issue, 58B, 857). The previously observed effects of amelogenins on the kinetics of apatite crystal growth and the morphology of OCP are described in the following references: Doi et al. 1984, J. Dent. Res., 63, 98; Aoba et al. 1987, Calcif. Tissue Int., 41, 281; Moradian-Oldak et al. 1998, Biopolymers, 46, 225; Hunter et al. 1999, Calcif. Tissue Int., 65, 226; Wen et al. 2000, J. Dent. Res., 79, 1902; Iijima et al. 2001, J. Crystal Growth, 222, 615; Iijima et al. 2002, J. Dent. Res., 81, 69.

One frequently employed system was seeded crystal growth of apatite in which extracted enamel or synthetic hydroxyapatite (HA) crystals were dispersed into SCSs containing 3–68 µg/ml of amelogenins (Aoba et al. 1987, Calcif. Tissue Int., 41, 281; Moradian-Oldak et al. 1998, Biopolymers, 46, 225;. Doi et al. (Doi et al. 1984, J. Dent. Res., 63, 98) concluded that the seeded enamel crystal growth was inhibited mainly by the central portion of the amelogenin molecule through their study of a series of bovine amelogenins of different molecular weights from 5,000 to 27,000. Aoba et al. (Aoba et al. 1987, Calcif. Tissue Int., 41, 281) and Moradian-Oldak et al. (Moradian-Oldak et al. 1998, Biopolymers, 46, 225) observed that the parent or the full-length amelogenin was found to have a slight inhibitory effect on apatite crystal growth most likely due to some adsorption affinity of its hydrophilic carboxy-terminal motif on apatite. The inhibition became insignificant after the proteolytic cleavage of this hydrophilic region. Additionally, rM179 appeared to have an adherence effect on growing apatite crystals, presumably through its molecular self-association (Moradian-Oldak et al. 1998, Biopolymers, 46, 225).

The coating of the present invention is typically applied in thin layers uniformly across the surface of the substrate. In certain embodiments, e.g., where the substrate to be coated is immersed in the amylogenin-containing calcifying solutions, the method allows for the uniform coating of complex surfaces including porous surfaces and recessed surfaces. The geometry of the substrate surfaces, which may be crucial to the effectiveness of the substrate upon implantation, should not be affected by immersion coating.

According to one embodiment of the method, the substrate is contacted with a supersaturated calcifying solution, wherein the solution comprises an effective amount of an amelogenin-type protein. An "effective amount" is an amount of amelogenin sufficient to substantially modify the growth of hydroxapatite or octacalcium phosphate crystals on the surface of the substrate. In one aspect a concentration of at least approximately 10 µg/ml amelogenin is used. Alternatively, concentrations greater than 100 µg/ml are used to profoundly modify the crystals.

The method is applied to a variety of substrates, including silicon, metals, ceramics and polymers. In particular, the method is useful for coating substrates which are intended for medical implantation, e.g., bone and dental prostheses. Such substrates are typically fashioned of strong biocompatible materials such as titanium metal. The method is compatible with other metals, including titanium alloy, tantalum, tantalum alloy, stainless steel and cobalt chromium alloy. Other well-known biocompatible materials such as ultra high molecular weight polyethylene, hydroxyapatite, Bioglass and Glass Ceramic A-W, may also be used.

In one aspect, the substrate is pre-treated prior to coating. Any treatment that modifies the surface of the substrate to facilitate crystal formation is a suitable pre-treatment, e.g., chemically treating the metal to form nanopockets. Titanium samples, for example, can be cleaned ultrasonically and "etched" prior to immersion in the supersaturated calcifying solution. Etching roughens the surface of titanium and facilitates crystal growth. Etching may be accomplished by various means including, without limitation, chemical, physical or thermal means. One example of chemical etching involves treatment of a metal, e.g., titanium, with hydrofluoric acid, followed by immersion in sodium hydroxide. In some embodiments, the substrate is well rinsed before contact with the calcifying solution. This method forms nano-sized pores on the surface of the substrate which facilitate the induction of calcium phosphate crystal growth. Other substrates, such as Bioglass, do not require hydrofluoric acid etching for crystal growth. One skilled in the art will recognize what steps are necessary to prepare the substrate for coating by referring to the literature in which the properties of the preferred implantable substrates are well-known and documented. Such steps are analogous to, and may include, crystal seeding and doping procedures.

The supersaturated calcifying solution of the invention comprises an aqueous solution having a pH in the range of about 5 to about 10, or alternatively a pH in the near-physiological range, e.g., about 6.5 to about 8. The solution contains at least calcium ions and phosphate ions, but may contain other ions, particularly physiologically relevant ions including, but not limited to, magnesium, sodium, chlorine, sulfate, potassium and carbonate. The pH of the solution may be maintained by a buffer such as Tris or any other chemical which provides effective buffering capability in the near-physiological pH range. The coating process is carried out typically at temperatures in the physiological range, e.g., approximately 35 to approximately 40 degrees Celsius, but may be carried out ambient temperatures from approximately 10 to approximately 35 degrees. In certain embodiments of the coating method, coating takes place at ambient atmospheric pressure.

Concentrations of ions in the supersaturated calcifying solution are in the range of, e.g., 100 to 200 mM $Na^+$, 3–5 mM $K^+$, 1–3 mM $Ca^{2+}$, 100 to 250 mM $Cl^-$, 1 to 2.5 mM $HPO_4^{2-}$, 1–2 mM $SO_4^{2-}$, and 1 to 100 mM Tris. The ionic strength of the solution is typically in the range of 100 to 200 mM, but useful coating may be achieved concentrations outside that range. The solution may be prepared by dissolving analytical grade chemicals, e.g., $CaCl_2.2H_2O$, $Ca(NO_3)_2.4H_2O$, $Na_2HPO_4.7H_2O$, NaCl, $KNO_3$, $KH_2PO_4$, in deionized water. One skilled in the art will recognize that other suitable compounds may be dissolved to achieve the same desired concentrations of ions. Other biologically relevant ions, such as magnesium or silicate, may be added or substituted for the ions listed above. Growth of the enamel-like biomaterial is primarily dependent on the presence of calcium and phosphate ions. Purified recombinant amelogenin or native amelogenin are first dissolved at higher concentrations in a buffered solution, then added to the calcifying solution to reach the desired final concentration. In another embodiment of the method, therapeutic agents including antibiotics, growth factors, or anti-inflammatory agents, are added to the supersaturated calcifying solution so that the agents are incorporated into the enamel-like coating.

The substrate, or a desired portion of the substrate, is immersed in the supersaturated calcifying solution for the length of time needed to produce the desired amount of enamel-like coating on the surface of the substrate. Typically, the substrate will be in contact with the solution for at least one hour, and more typically for one to seven days. The length of time will vary depending on such recognizable factors as the amount of coating desired, the particular concentrations of ions present in the calcifying solution, the particular amount of amelogenin present, peculiarities of the substrate surface, the solution pH and the ambient temperature and pressure.

In one embodiment of the coating method, the substrate to be coated is first contacted with a supersaturated calcifying solution which is substantially free of any amelogenin-type protein. As used herein, the term "substantially free" comprises any concentration that will not affect crystal formation. In one aspect, amelogenin-like proteins are not present in the solution, or are present only in insignificant concentrations (e.g., 1 µg/ml or less). As is apparent to those skilled in the art—the specific amount of protein that can be present without affecting crystal formation varies with the substrate, the solution, the pH, ionic strength and the concentration of protein contained within the second contacting solution. After a period of incubation in contact with this first solution, the substrate is contacted with the amelogenin-containing solution discussed above. The first amelogenin-free solution may comprise ions and ion concentrations similar to the solution containing amelogenin. Typically, the first amelogenin-free solution will comprise higher concentrations of $K^+$ (e.g., between 75 and 200 mM) and NO3- (e.g., between 75 and 200 mM) and approximately half the concentration of $Ca^{2+}$ and $HPO_4^{2-}$. According to this embodiment, the first incubation continues at 37 degrees Celsius for 1 to 24 hours, but typically between 2 and 10 hours or between 3 and 5 hours.

The methods described above yield a novel enamel-like biomaterial, the properties of which are influenced by the presence of the amelogenin-type protein in the calcifying solution. As natural enamel in the body is characterized by the presence of elongated crystals, practitioners of the method will frequently desire that the synthetic enamel-like coating also comprises elongated crystals. The methods disclosed herein are capable of creating enamel-like coatings which consist of submicron bundles of elongated apatite crystals with an average aspect ratio (length/width) of at least two. In addition, analysis of the reactions shows that the resultant coating comprises approximately $1 \times 10^{-4}\%$ to 10% w/w amelogenin-type protein.

Without further elaboration, it is believed that one skilled in the art can follow the preceding description and utilize the present invention to its fullest extent. The following examples of specific embodiments are, therefore, to be construed as merely illustrative and are not intended to limit the disclosure in any way.

EXAMPLES

Example 1

Coating of Titanium with Enamel-like Biomaterial Comprising Amelogenin

Materials and Methods. Recombinant murine amelogenin rM179 was expressed, purified and characterized as previously described (Simmer et al. 1994, Calcif Tissue Int, 54, 312–319). The rM179 protein is analogous to the secreted full-length mouse amelogenin M180 lacking only the amino-terminal Met1 and phosphorylation of Ser16 (Fincham et al. 1993, Biochem Biophys Res Comm, 197, 248–255). Bovine serum albumin (BSA) purchased from Sigma Chemicals (A-4503, Lot77H0504) was used as a control protein for inhibitory activity, which has been well documented previously (Robinson et al. 1992, J Dent Res, 71, 1270–1274; Radin et al. 1996, J Biomed Mater Res, 30, 273–279). Titanium samples of 10×10×1.3 mm were cut from the commercially pure titanium sheet (Titanium Industries, Grade 2, ASTM B265). Two types of SCSs were prepared from analytical-grade $CaCl_2.2H_2O$, $Ca(NO_3)_2.4H_2O$, $Na_2HPO_4.7H_2O$, NaCl, $KNO_3$, $KH_2PO_4$ to achieve the ion concentrations listed in Table 2.

SCSs containing rM179 or BSA were made by dissolving the protein into the blank SCSs at concentrations ranging from 12.5 to 100 µg/ml. Titanium samples were ultrasonically cleaned in distilled-deionized water (DDW), acetone, 70% ethanol solution for 20 min each, and in DDW again for 10 min. The cleaned samples were etched with 10 ml 10% HF solution for 30 min, immersed in 40 ml 2 N NaOH solution at 85° C. for 5 h and completely rinsed with DDW. Two SCSs (SCS1 and SCS2) were employed for growing apatite crystals on the chemically modified titanium. The pH of SCS1 was 7.4 at room temperature and that of SCS2 was maintained to be 7.4 at 37° C. by using a Metrohm 718 pH-STAT during the crystal growth experiments. The OCP and apatite crystal growth on titanium was respectively achieved through the following two processes. Process I: Immersion of the chemically treated titanium samples in blank, rM179- or BSA-containing SCS1—(20 ml per sample at 37° C. for 1 d). Process II: Pre-incubation of the samples in blank SCS1—(20 ml per sample at 37° C. for 4 h) followed by an immersion in blank, rM179- or BSA-containing SCS2—(40 ml per sample at 37° C. for 3 d).

The protein concentrations of those SCSs containing rM179 and BSA before and after the crystal growth experiments were measured using reverse phase high performance liquid chromatography (HPLC, Vydac, C4-214TP54 column, Separations Group, Hesperia, Calif., USA). All the samples were rinsed with DDW, air-dried, and characterized by means of X-ray diffraction (XRD, Rigaku, Cu Kα radiation at 50 kV/70 mA), scanning electron microscopy (SEM, Cambridge 360, at 15 kV), and transmission electron microscopy (TEM, JOEL, JEM-1200EM) coupled with selected area electron diffraction (SAED), as previously described (Wen et al. 2000, J Biomed Mater Res, 52, 762–773).

Results. SEM micrographs of an untreated (as received) titanium surface, and those after HF and NaOH treatment are shown in FIG. 1. It was noted that the HF etching increased the roughness of titanium surface for the emerging of nanosized structures (FIG. 1b). Nano-sized pores were formed at the sample surface by the subsequent NaOH immersion (FIG. 1c). The two-step chemical treatment of titanium samples was performed to create a bioactive—Ca—P inductive—surface. All the samples were completely coated by a mineral layer after different immersion procedures as indicated by their representative XRD patterns in FIG. 2. The formation of a nanometer scaled porous oxide layer formed at titanium surface after the chemical treatment was the key to the mineral initiation from the SCS1 (Wen et al. 1998, J Mater Sci Mater Med, 9, 121–128; Wen et al. 1998, J Crystal Growth, 186, 616–623).

Figure 2:
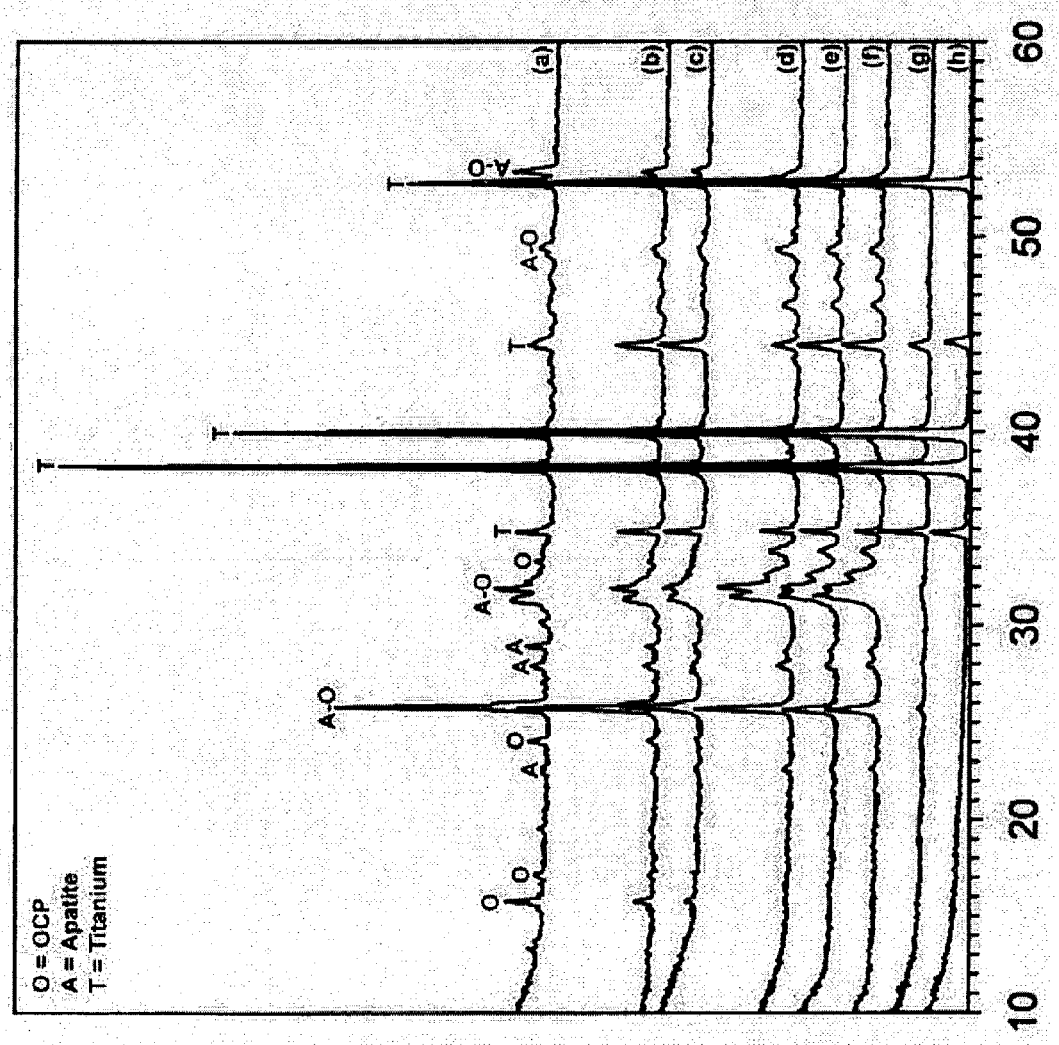
FIG. 2 shows XRD (X-ray diffraction) patterns of Ca—P formed on chemically modified titanium via Process I (a–c) at: (a) no protein, (b) 100 μg/ml rM179 and (c) 100 μg/ml BSA and Process II (d–f) at: (d) no protein, (e) 100 μg/ml BSA and (f) 100 μg/ml rM179. The patterns (g) and (h) were from samples after 4 h of SCS1 immersion and from chemically modified titanium, respectively. The diffraction peaks were assigned according to the standard JCPDS cards (1980, JCPDS International Center for Diffraction Data. Powder Diffraction File. Swarthmore, Pa.).

As determined by the X-ray diffraction patterns in FIG. 2 a very thin layer of apatite was nucleated on the sample surface followed by the growth of OCP crystals in Process I (FIG. 2a–c) while apatite was the only mineral phase developed in Process II (FIG. 2d–f). Only titanium peaks were detected in the pattern of chemically modified titanium (FIG. 2h) but apatite crystals were formed after 4 h immersion in blank SCS1 (FIG. 2g). The XRD patterns of OCP/apatite formed from Process I (FIG. 2a–c) were similar to one another regardless of the presence of different concentrations of different proteins, so were the XRD patterns of apatite formed from Process II (FIG. 2d–f).

Figure 3:
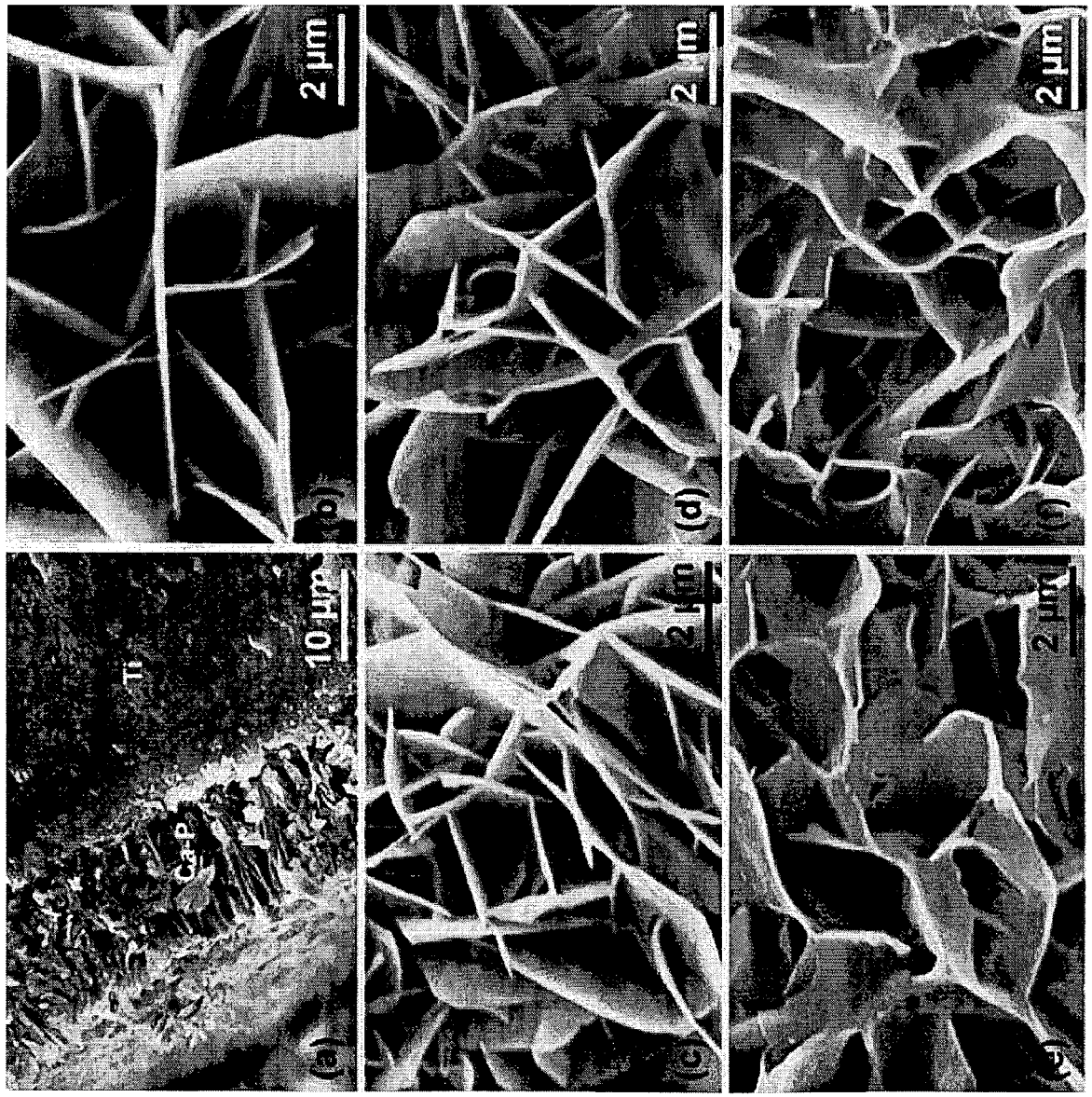
FIG. 3 shows SEM micrographs of the cross section (a) of the Ca—P coating formed on the chemically modified titanium (Ti) via Process I and the morphologies of OCP crystals formed at (b) no protein, (c) 50 and (d) 100 μg/ml rM179, (e) 50 and (f) 100 μg/ml BSA.

FIG. 3 represents the SEM micrographs of the cross sections of the Ca—P coatings (FIG. 3a) and the morphology of OCP crystals formed on the chemically modified titanium by process I, in the absence (FIG. 3b), and presence of amelogenin (FIG. 3c–d) and albumin (FIG. 3e–f). After 1 day of immersion in blank SCS1 about 15-µm thick OCP crystal layer was precipitated on titanium. The crystals were seen in the characteristic plated-like shape of OCP and measured ~200 nm thick and several microns across (FIG. 3b). The application of rM179 showed no significant inhibitory effect on either the morphology or sizes of OCP crystals over the concentration range of 12.5–100 µg/ml (FIG. 3c–d), whereas the presence of BSA significantly altered the plated-like OCP crystals into a round edged, curved shape indicating a general inhibitory effect (FIG. 3e–f).

Figure 4:
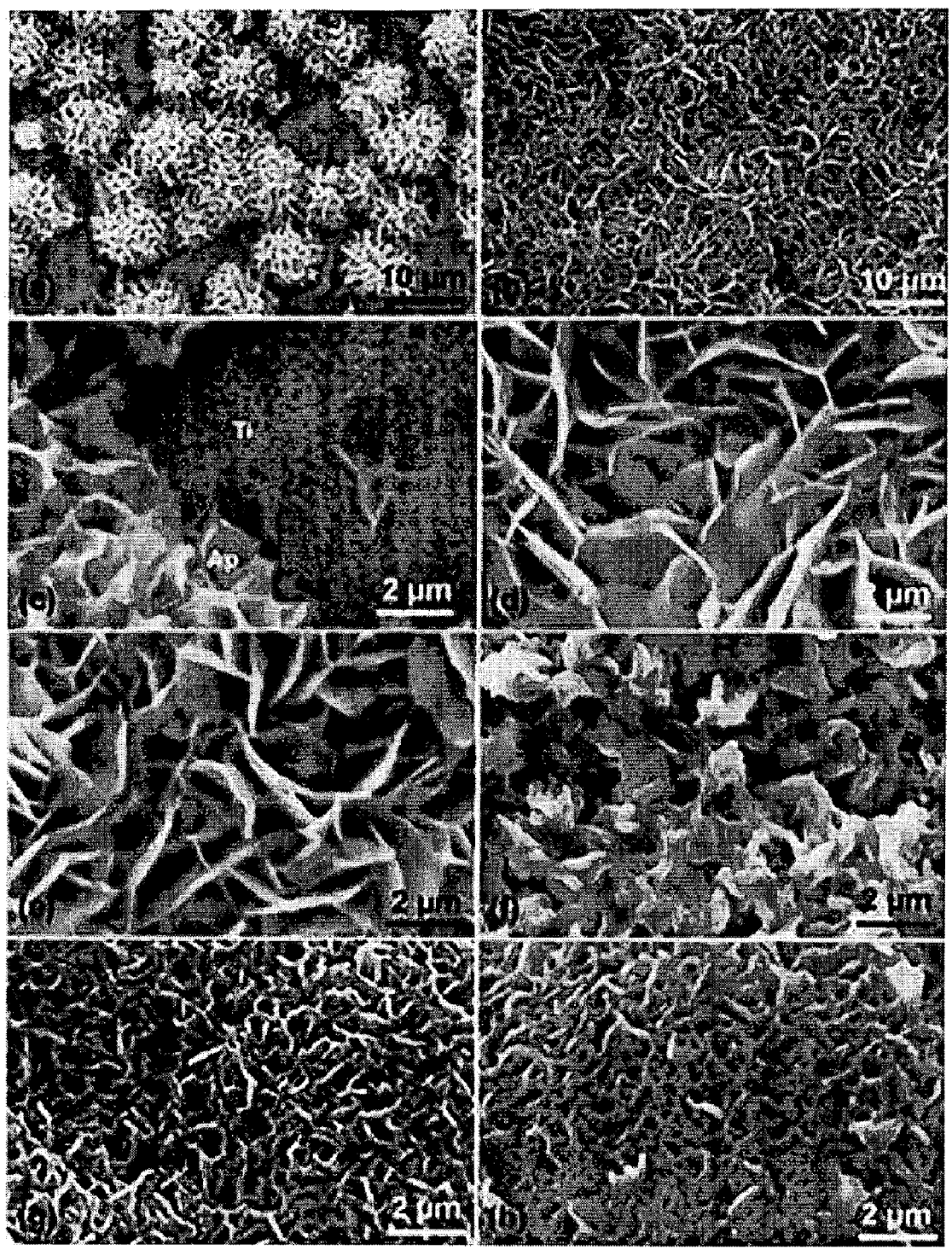
FIG. 4 shows SEM micrographs of apatite (Ap) crystals initially induced by chemically modified titanium (Ti) after 4 h SCS1 immersion (a, c) and apatite coatings formed via Process II at (b, d) no protein, (e) 50 and (f) 100 μg/ml rM179, (g) 50 and (h) 100 μg/ml BSA. Images at (c) and (d) are respectively the higher magnifications of (a) and (b).
Figure 5:
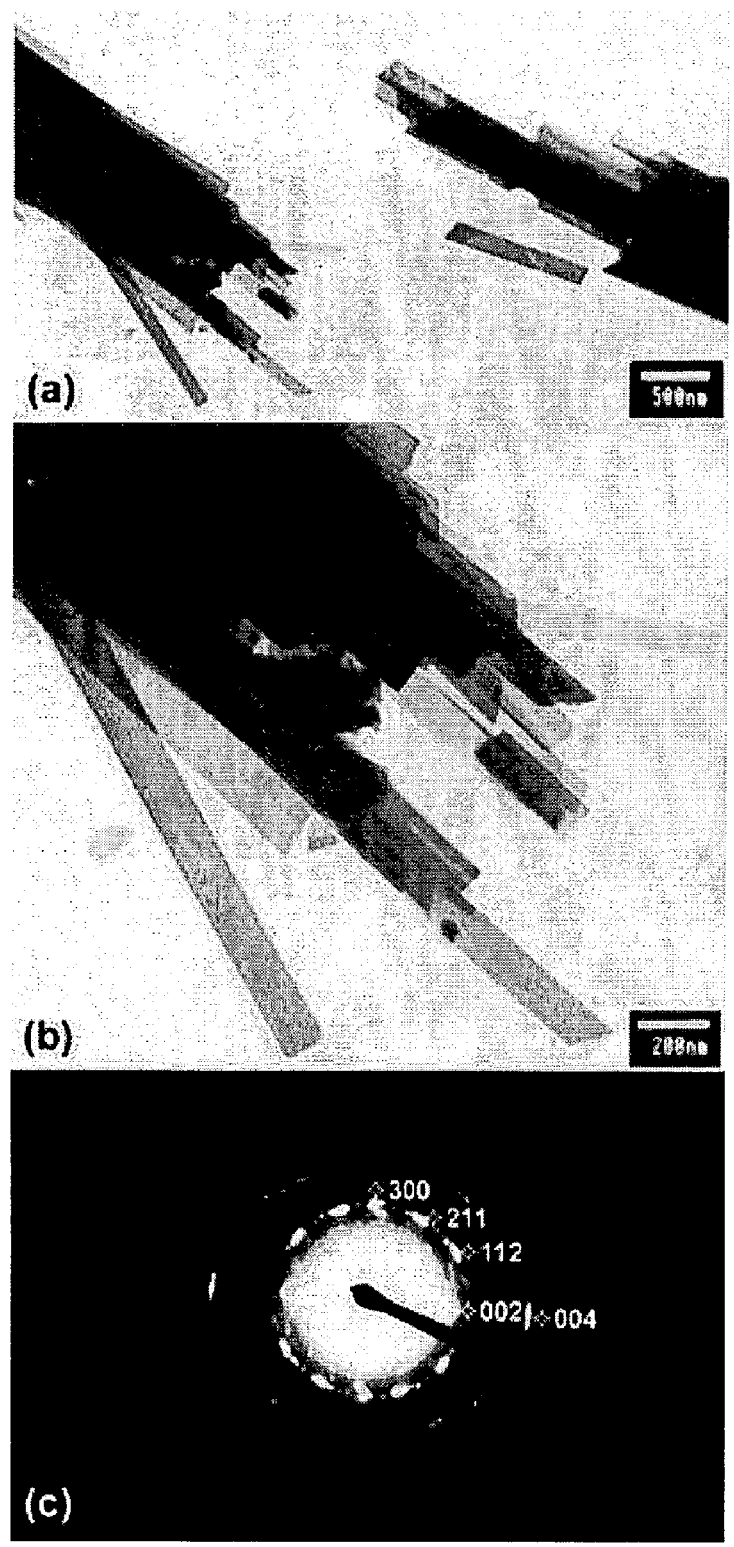
FIG. 5 shows TEM images (a) of the apatite crystals formed via Process II in the presence of 100 μg/ml of rM179. The enlargement of the left bundle of crystals in (a) was shown in (b) and the corresponding SAED was shown in (c). The SAED pattern of apatite was indexed according to the standard JCPDS cards (1980, JCPDS International Center for Diffraction Data. Powder Diffraction File. Swarthmore, Pa.).

FIG. 4 is the SEM micrographs of apatite crystals grown by process II in the absence (FIG. 4a–d) and the presence of amelogenin (FIG. 4e–f) and albumin (FIG. 4g–h). The apatite crystals developed from Process II without applying any proteins were observed under SEM to be in a slightly curved platy shape, mostly less than 2 µm across (FIG. 4a–d). Regardless of the concentration applied, BSA showed dramatic inhibition as indicated by the significantly reduced crystal sizes (FIG. 4g–h). Interestingly, the effects of rM179 appeared to be dose dependent. No significant effect was observed at a concentration of 50 µg/ml (FIG. 4e). However, at higher concentration, e.g., 100 µg/ml, amelogenin remarkably modulated the plated-like crystals into submicron-sized structures (FIG. 4f). These were characterized by TEM in combined with SAED to be bundles of elongated apatite crystals with a preferential orientation of 002 (c-axis) (FIG. 5).

Table 3 summarizes the consumption rate (%) of recombinant amelogenin rM179 and BSA during OCP and apatite crystal growth on titanium surface. rM179 is consumed during the OCP and apatite crystal growth very differently from BSA. There was more BSA absorbed by OCP crystals than apatite crystals while much more rM179 was incorporated into the apatite than OCP crystal layers.

TABLE 2

Concentrations (mM) of ions present in the PBS and two SCSs employed for Ca-P crystal growth on biomaterials.

| Ion | SCS1 | SCS2 |
|---|---|---|
| $Na^+$ | 136.8 | — |
| $K^+$ | 3.71 | 144.6 |
| $Ca^{2+}$ | 3.10 | 1.5 |
| $Cl^-$ | 185.5 | — |
| $HPO_4^{2-}$ | 1.86 | 0.9 |
| $NO_3^-$ | — | 145.8 |
| Tris | 50 | |

TABLE 3

Consumptions (%) of rM179 and BSA during OCP and apatite crystal growth on titanium analyzed by HPLC.

| Protein | OCP | Apatite |
|---|---|---|
| rM179-50 µg/ml | 27 | 97.5 |
| rM179-100 µg/ml | 22.5 | 78 |
| BSA-50 µg/ml | 32 | 7 |
| BSA-100 µg/ml | 25 | 9 |

Example 2

Coating of Bioglass® with Enamel-like Material Comprising Amelogenin

Materials and Methods. Bioactive (Ca—P inducible) materials may serve as the substrates for apatite crystal growth from SCSs. One of these advanced biomaterials is bioactive glass, which induces apatite formation by immersion in a buffer solution of Tris-HCl or phosphate buffered saline (PBS) (Zhong et al. 1997, Transactions of the 23rd Annual Meeting of the Society for Biomaterials, 125). 45S5 type Bioglass® discs were provided by USBiomaterials Corporation. This material has been clinically applied for over 7 years as bone graft materials, especially in periodontal defect repair (Hench 1994, Bioceramics 7, Ö. H. Andersson, and A. Yli-Urpo (Eds.), Butterworth-Heinemann Ltd., Oxford, 3; Hench et al. 1996, Life Chem. Rep., 13, 187).

A PBS and two SCSs (SCS1 and SCS2) were employed for growing apatite crystals on the Bioglass discs. The detailed compositions of PBS, SCS1 and SCS2 are listed in Table 4. The pH of both PBS and SCS1 were 7.4 at room temperature and that of SCS2 were always maintained to be 7.4 at 37° C. The rM179 and rP172 proteins were prepared as previously described by Simmer et al. (Simmer et al. 1994, Calcif. Tissue Int., 54, 312) and Ryu et al. (Ryu et al. 1999, J. Dent. Res., 78, 743). Bovine serum albumin (BSA) was used as a control protein for inhibitory activity, which has been well documented previously (Radin et al. 1996, J. Biomed. Mater. Res., 30, 273; Gilman et al. 1994, J. Inorganic. Biochem., 55, 3142–44). The concentration applied in the SCSs for all the proteins was 50 µg/ml. The apatite crystal growth on Bioglass was achieved in the following two ways: (1) Direct Immersion: Immersing the samples in blank and rP172-containing SCS1 (SCS1$_b$ and SCS1$_{rM172}$) at 37° C. for 0.5, 1, 2 or 4 h; (2) PBS Pre-incubation: Incubating the samples in PBS at 37° C. for 1 week followed by immersions in blank, BSA- or rM179-containing SCS2 (SCS2$_b$, SCS2$_{BSA}$ and SCS2$_{rM179}$) at 37° C. for 3 d.

TABLE 4

Concentrations (mM) of ions present in the PBS and two SCSs employed for Ca-P crystal growth on biomaterials

| Ion | PBS | SCS1 | SCS2 |
|---|---|---|---|
| Na$^+$ | 157.2 | 136.8 | — |
| K$^+$ | 4.44 | 3.71 | 144.6 |
| Ca$^{2+}$ | — | 3.10 | 1.5 |
| Cl$^-$ | 139.6 | 185.5 | — |
| HPO$_4^{2-}$ | 11.9 | 1.86 | 0.9 |
| NO$_3^-$ | — | — | 145.8 |
| Tris | — | 50 | — |

Direct Immersion. The surface transformation of Bioglass observed in SCS1$_b$ was in a good consistence with the general reaction sequence occurred at bioactive glass surfaces during implantation or in vitro immersion (Hench 1998, J. Am. Ceram. Soc., 81, 1705). The smooth sample surface as imaged by atomic force microcopy (AFM) (FIG. 6A) was changed to be very rough after 0.5 h of immersion because of the glass network dissolution. Spherical silica-gel particles with diameters of 150–300 nm consisting of substructures of 20-60 nm across were formed after 1 h of immersion. The chemisorption of amorphous Ca—P and crystallization of nanophase apatite occurred epitaxially on the silica-gel structures during 1–4 h of immersion. The presence of rP172 dramatically modulated the Bioglass surface reaction during SCS1$_{rP172}$ immersion. In the first 0.5 h of immersion, more than 95% of rP172 protein in solution was adsorbed onto the sample surfaces as determined by analytical reverse phase high performance liquid chromatography (HPLC). It was indicated in FIG. 6B that the protein self-assembled into spherical assemblies of 10–60 nm in diameters. During 0.5–4 h Of SCS1$_{rP172}$ immersion, the protein assemblies of rP172 remarkably induced the formation of orientated silica-gel plates (about 100 nm wide and 50 nm thick) and subsequently of platy apatite minerals (FIG. 6D), which were obviously different from those formed in SCS1$_b$ (FIG. 6C). Under TEM, the apatites grown after 2–4 h of SCS1$_b$ immersion were revealed to be rod crystals that measured about 100 nm thick and 500 nm long. However, it appeared that the crystals formed after 2–4 h of SCS1$_{rP172}$ immersion all adopted an elongated shape. They were in a length comparable to the crystals formed in SCS1$_b$ but significantly reduced thickness only about 5–7 nm. The highly organized long and thin crystals observed after 4 h Of SCS1$_{rP172}$ immersion strikingly resembled the apatite crystals observed in the early stage of enamel biomineralization (Fincham et al. 1995, J. Struct. Biol., 115, 50; Diekwisch et al. 1995, Cell Tissue Res., 279, 149).

Figure 6:
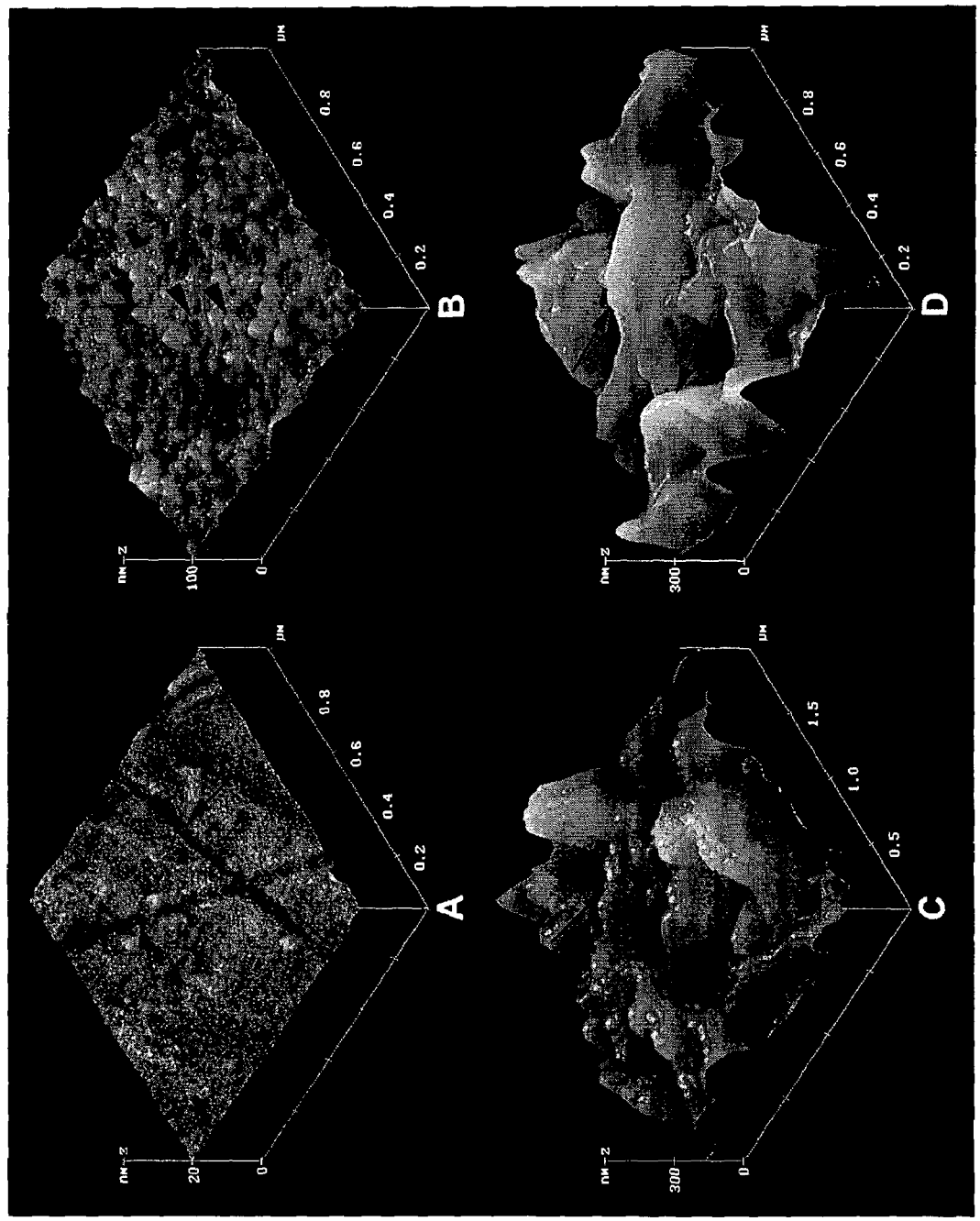
FIG. 6 shows Tapping Mode AFM images of the untreated (as received) Bioglass surface (A) and those after 0.5 h of immersion in $SCS1_{rp172}$ (B) and 4 h of immersion in $SCS1_b$ (C) and $SCS1_{rP172}$ (D). Arrows denote polishing scratches in A, apatite mineral in C and D; arrowheads indicate nano-sphere assemblies in B.
Figure 7:
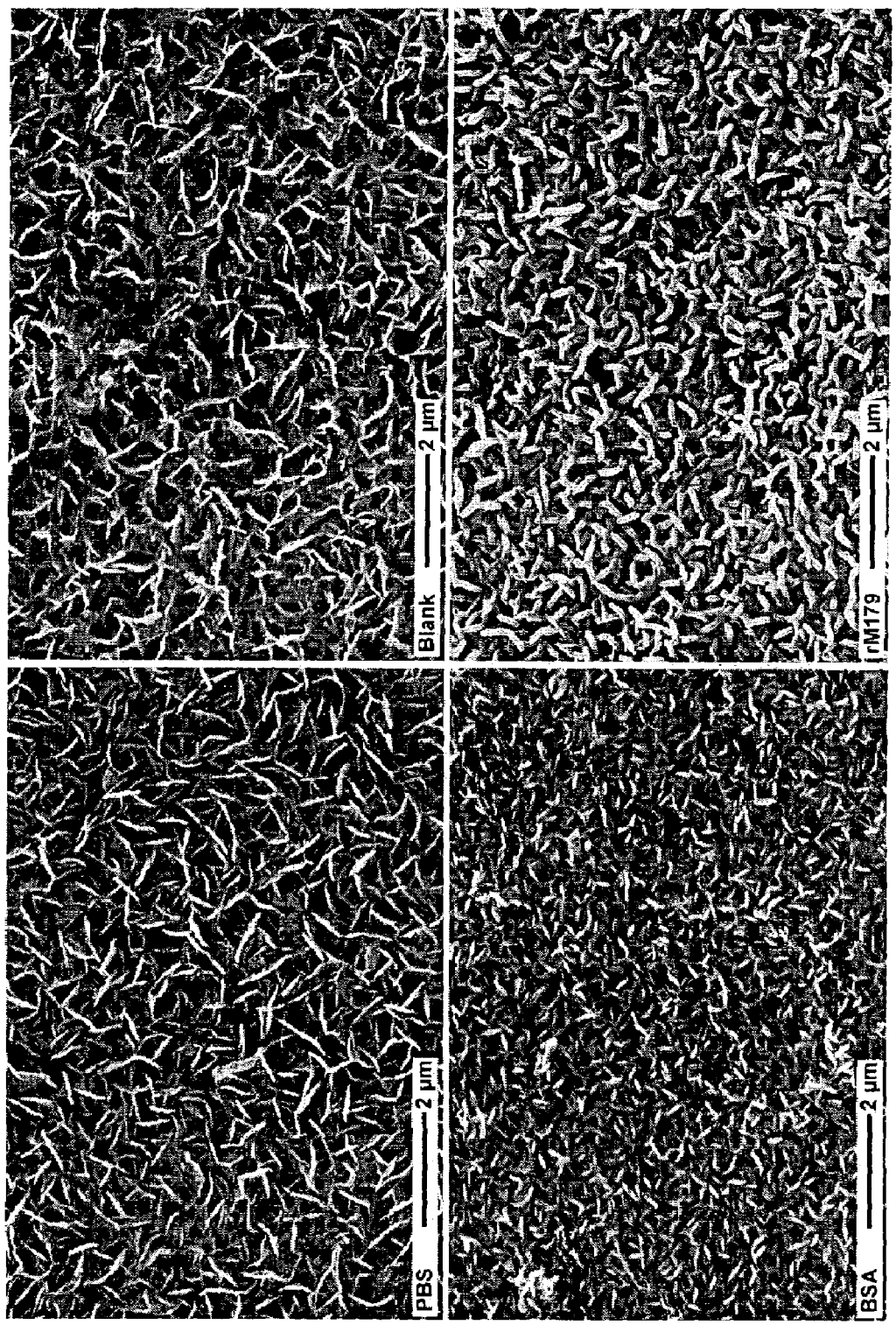
FIG. 7 shows SEM micrographs of the apatite crystals formed on Bioglass samples after incubation in PBS for 1 week and subsequent immersion in blank, BSA- and rM179-containing SCS2 for 3 days.

PBS Pre-incubation. Mineral layers precipitated on all the treated samples were characterized to be apatite by X-ray diffraction (XRD) and Fourier transmission infrared spectroscopy (FTIR). FIG. 6 presents scanning electron microscopy (SEM) images of the apatites formed after different immersions. Plate-shaped crystals (~50 nm thick and 300–600 nm across) were observed on the samples after PBS incubation. The crystals grown from SCS2$_b$ were of the typical plate shape except for a slight increased thickness, while needle-shaped crystals (200–300 nm long and 50–70 nm thick) were precipitated on the SCS2$_{BSA}$ immersed samples. It was surprising to observe that the apatites deposited on the SCS2$_{rM179}$-immersed samples adopted an elongated, curved shape (~500 nm long and ~120 nm thick). They were revealed by transmission electron microscopy (TEM) to be bundles of lengthwise crystals (15–20 nm thick) orientated parallel to one another, much alike the long and thin crystals observed in the very early stage of tooth enamel formation (Fincham et al. 1995, J. Struct. Biol., 115, 50; Diekwisch et al. 1995, Cell Tissue Res., 279, 149). The modulating effects of rM179 on apatite crystals are distinctly different from the overall inhibition of BSA.

Atomic force microscopic study has revealed a progressive accretion of rM179 molecules during nanospheres assembly in a Tris-HCl buffer at concentrations from 12.5 to 300 µg/ml (Wen et al. 2001, Matrix Biol, 20, 387–395). At low concentrations (12.5–50 µg/ml), nanospheres with diameters varying from 7 to 53 nm were identified while at concentrations between 100–300 µg/ml the size distribution was significantly narrowed so that nanosphere diameters were consistently between 10 and 25 nm. These nanospheres were observed to be the basic building blocks of both engineered rM179 gels and the developing enamel extracellular matrix. We infer that the stable 15–20 nm nanosphere structures generated in the presence of high concentrations of amelogenins may be of great importance in creating a highly organized ultrastructural microenvironment required for the formation of initial enamel apatite crystallites or synthesizing materials having enamel-like structures.

What is claimed is:

1. A method for modifying the growth of apatite crystals onto a biocompatible substrate comprising:
    adding an effective concentration of an amelogenin protein to a supersaturated calcifying solution and
    contacting the substrate with the supersaturated calcifying solution under suitable conditions until oriented and organized crystal growth is achieved.

2. The method of claim 1, wherein the modification of crystals is a reduction in crystal size and an increase in the average aspect ratio (1/w) of the crystals to approximately two or greater.

* * * * *

UNITED STATES PATENT AND TRADEMARK OFFICE
CERTIFICATE OF CORRECTION

PATENT NO. : 7,132,015 B2  
APPLICATION NO. : 10/371678  
DATED : November 7, 2006  
INVENTOR(S) : Hai Bo Wen et al.

Page 1 of 1

It is certified that error appears in the above-identified patent and that said Letters Patent is hereby corrected as shown below:

In the Specification

Column 1, Lines 16-18:
After section heading "STATEMENT AS TO INVENTION RIGHTS UNDER FEDERALLY SPONSORED RESEARCH"
Delete:
"This invention was made with government support under Grant Nos. P01 DE002848 and R29 DE012350, awarded by the National Institutes of Health (NIH). The government has certain rights in the invention."
Insert:
--This invention was made with government support under Grant Nos. DE013414 and DE012350, awarded by the National Institutes of Health (NIH). The government has certain rights in the invention."--

Signed and Sealed this  
Twenty-first Day of September, 2021

Drew Hirshfeld  
*Performing the Functions and Duties of the  
Under Secretary of Commerce for Intellectual Property and  
Director of the United States Patent and Trademark Office*